United States Patent [19]

Moore

[11] 4,248,225

[45] Feb. 3, 1981

[54] GAUGE DEVICE FOR HYPODERMIC SYRINGES

[76] Inventor: Fred J. Moore, 1264 N. Dale St., St. Paul, Minn. 55117

[21] Appl. No.: 10,528

[22] Filed: Feb. 9, 1979

[51] Int. Cl.³ ............................................. A61J 1/06
[52] U.S. Cl. ............................................. 128/218 C
[58] Field of Search ............ 128/218 R, 218 C, 215, 128/216, 234

[56] References Cited

U.S. PATENT DOCUMENTS

| | | | |
|---|---|---|---|
| 2,863,452 | 12/1958 | Ogle, Sr. | 128/218 C |
| 3,610,241 | 10/1971 | LeMarie | 128/218 C X |
| 3,770,026 | 11/1973 | Isenberg | 128/218 C X |

Primary Examiner—John D. Yasko
Attorney, Agent, or Firm—Williamson, Bains, Moore & Hansen

[57] ABSTRACT

A gauge device for a hypodermic syringe may be readily applied to the flanged end of the hypodermic syringe barrel. The gauge device includes a rigid bar which is spaced a predetermined distance from the free end of the plunger of the hypodermic syringe when the plunger is fully extended into the syringe barrel. The bar limits the retractive movement of the plunger from the barrel and therefore limits filling of the hypodermic syringe to a predetermined dosage.

1 Claim, 5 Drawing Figures

U.S. Patent        Feb. 3, 1981        4,248,225
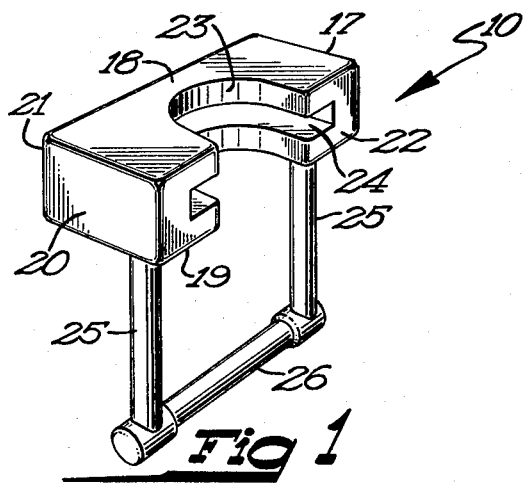
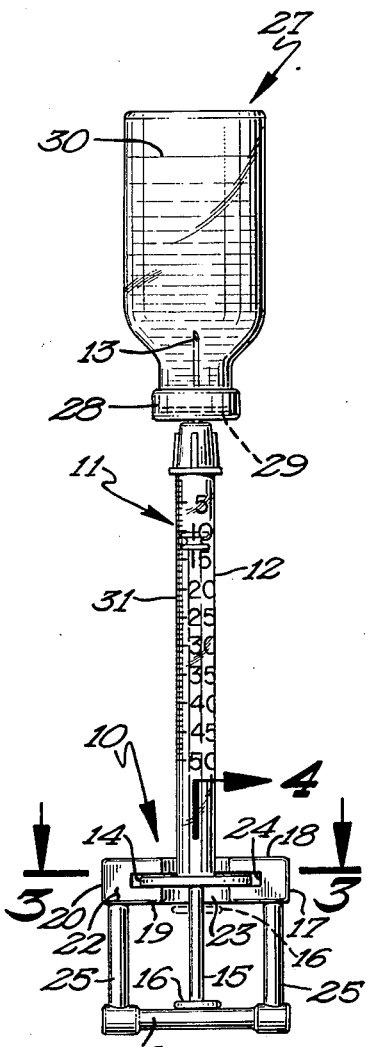
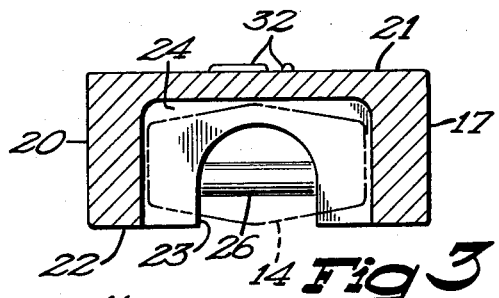
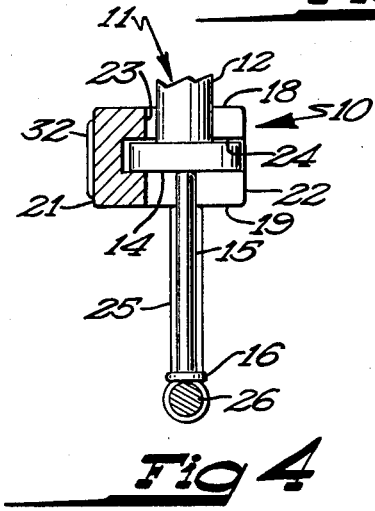
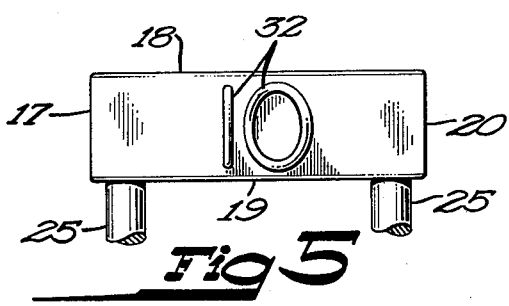

GAUGE DEVICE FOR HYPODERMIC SYRINGES

SUMMARY OF THE INVENTION

This invention relates to a gauge device for hypodermic syringes and the like.

Persons suffering from diabetes and other chronic diseases are typically required to make daily self-administered injections of drugs such as insulin. Quite often, sufferers of diabetes experience impairment of their eyesight, and it is difficult for such persons having poor eyesight to make accurate injection measurements. It will be appreciated that accurate dosages of these injections is absolutely essential.

It is therefore a general object of this invention to provide a gauge device, of simple and inexpensive construction, which may be readily applied to a hypodermic syringe to permit filling of the syringe with a predetermined accurate dosage.

More specifically, the gauge device is of single piece construction, and when applied to a hypodermic syringe, limits the retractive movement of the plunger during the filling step to the precise, predetermined dosage thereby permitting accurate filling of the syringe without requiring the user to visually read the dosage scale.

These and other objects and advantages of this invention will more fully appear from the following description made in connection with the accompanying drawings, wherein like reference characters refer to the same or similar parts throughout the several views.

FIGURES OF THE DRAWINGS

FIG. 1 is a perspective view of the novel gauge device;

FIG. 2 is a side elevational view of the gauge device applied to a conventional hypodermic syringe during the filling step;

FIG. 3 is a cross-sectional view taken approximately along line 3—3 of FIG. 2 and looking in the direction of the arrows;

FIG. 4 is a cross-sectional view taken approximately along line 4—4 of FIG. 2 and looking in the direction of the arrows; and FIG. 5 is a fragmentary elevational view of a portion of the gauge device.

DESCRIPTION OF THE PREFERRED EMBODIMENT OF THE INVENTION

Referring now to the drawings and more particularly to FIG. 1, it will be seen that one embodiment of the novel gauge device, designated generally by the reference numeral 10, is thereshown. The gauge device is adapted to be used with a hypodermic syringe 11 which includes an elongate cylindrical barrel 12 having a needle 13 secured to one end thereof. The other end of the cylindrical barrel is provided with a flange 14, and an elongate plunger 15 is movable in the barrel. The outer or free end of the plunger 15 is provided with a flange 16, as best seen in FIG. 2. As pointed out above, the hypodermic syringe 11 is of conventional construction and is typically the kind used by persons suffering from diabetes in making insulin injections.

The gauge device 10 includes a barrel engaging member 17 which is of generally rectangular configuration and includes a substantially, flat upper surface 18, a flat lower surface 19, substantially flat parallel end surfaces 20, a side surface 21, and a side surface 22. The gauge device, including the barrel engaging member, may be made of any suitable rigid material, such as plastic, metal or the like. The barrel engaging member 17 has an arcuate recess 23 therein which extends inwardly from the side surface 22 and through the upper surface 18 and lower surface 19. It will be noted that the arcuate recess 23 is generally centrally located with respect to the end surfaces 20. The barrel engaging member 17 also has a slot 24 therein which extends inwardly from the side surface 22.

A pair of elongate, substantially identical rigid, connecting members 25 are rigidly connected to the lower surface 19 of the barrel engaging member and project therefrom. The connecting elements 25 are also rigidly connected to an elongate rigid plunger engaging element 26. Referring now to FIG. 3, it will be seen that the plunger engaging element 26 is generally centrally located with respect to the recess 23.

As pointed out above, the hypodermic syringe 11 is typically used by persons suffering from diseases that require daily injections such as diabetes and the like. Referring now to FIG. 2, it will be seen that the hypodermic syringe 11 is illustrated during the syringe filling step prior to making an injection. The drug, such as insulin 30, is contained within a bottle or vial 27 of well known construction having a top 28 provided with a puncturable membrane 29. The syringe barrel 12 is provided with a scale and number indicia 31 to permit a user to visually determine the desired dosage during the filling step. However, when visual perception of this scale is not possible by persons with impaired eyesight, the novel scale device 10 permits such users to accurately fill the syringe to the desired level.

During the syringe filling operation, the user will take the hypodermic syringe 11, preferably in his left hand, and will grip the selected gauge device 10 in his right hand and insert the flange 14 of the cylindrical barrel into the slot 24.

In this regard, each user will have a set of the gauge devices, each gauge device corresponding to a predetermined dosage. Thus, the spacing between the surface 19 of the barrel engaging member and the lower surface of the plunger engaging element 26 will vary according to the predetermined dosage. In order to identify the gauge dosage for each gauge device 10, a raised number will be provided for each gauge device 10 and will be located on the surface 21 as best seen in FIG. 5. It will be seen that the number indicia 32 is sufficiently raised to permit a user to determine the numerical value by touch in the manner of braille.

When the flange 14 is seated in slot 24, the user may retain the syringe in seated relation in the barrel engaging member by gripping the barrel engaging member between his right thumb and first two fingers. The syringe plunger will then be retracted until the flanged end 16 of the plunger engages the plunger engaging element 26. When the plunger is retracted, air will be introduced into the barrel 12.

The user will then insert the needle of the hypodermic syringe through the membrane 29 and into the bottle 27 containing the insulin 30. The bottle or vial 27 and the syringe may be held in the left hand by the user. The user will then move the plunger from its retracted position to its fully extended position into the barrel thereby injecting air into the bottle or vial 27. Thereafter, the user may retract the plunger until the flanged end 16 of the plunger again engages the plunger engaging element 26 and the syringe will be filled with ten units of insulin and is ready for body injection.

As the user's dosage changes, the user will select the particular gauge device which corresponds to the correct dosage. The user may readily determine the correct gauge device by feeling the raised number (or other indicia) located on the barrel engaging member 17. The gauge device may be readily applied and removed from a hypodermic syringe and involves no moving parts nor does it interfere in any way with the use of the hypodermic syringe. This gauge device provides the user with a means for obtaining the precise correct dosage for the injection even though the user has totally impaired vision.

Thus, it will be seen that I have provided a novel gauge device for hypodermic syringes which not only is of simple and inexpensive construction and operation, but one which functions in a more efficient manner than any heretofore known comparable device.

I anticipate that various changes can be made in the size, shape and construction of the gauge device for hypodermic syringes disclosed herein without departing from the spirit and scope of my invention as defined by the following claims.

What is claimed is:

1. A gauge device for a hypodermic syringe for use by persons with impaired vision, the syringe including an elongate barrel having a needle at one end and having a flange projecting laterally outwardly from the other end thereof, an elongate plunger extending into the barrel and projecting outwardly therefrom, the plunger being extensible into and retractable from the barrel, said gauge device comprising:

a generally rectangular shaped barrel engaging member having opposed end surfaces, opposed side surfaces, and opposed upper and lower surfaces, an arcuate recess in said barrel engaging member extending inwardly from one side surface thereof, a slot in said barrel engaging member extending inwardly from said one side surface and completely receiving therein the flange of the barrel of the syringe when the barrel is positioned within the recess, a pair of similar spaced apart, elongate, rigid connecting members each being rigidly connected at one end thereof to the barrel engaging member adjacent one of said end surfaces and projecting downwardly from said lower surface, an elongate plunger engaging element extending between and being rigidly connected to the other end of each of said connecting members and being disposed in obstructing relation with the outer end of the plunger of the syringe to limit retractive movement of the plunger when the barrel engaging member is applied to the syringe, the plunger of the syringe being unobstructed in its movement between a retracted position when the outer end of the plunger engages the upper surface of the plunger engaging element, and a fully extended position, whereby a user when gripping the gauge device with one hand will obstruct the slot in the barrel engaging member the plunger of the syringe will be retracted from the fully extended position, to engage the plunger engaging member, then extended into the barrel after the needle of the syringe is inserted into a container containing a drug, and the plunger may thereafter be retracted to engage the plunger engaging member so that a dosage of predetermined volume is obtained, and a raised dosage designating number on the side surface of said barrel engaging member opposite the slotted side surface, said raised dosage designating number being capable of being perceived by touch by a user and indicating the dosage when the plunger of the syringe is in the retracted position.

* * * * *